United States Patent [19]

Thongpreda et al.

[11] Patent Number: 5,507,829
[45] Date of Patent: Apr. 16, 1996

[54] SET OF FIXATION STEMS HAVING SIMILAR STIFFNESS

[75] Inventors: Nisra Thongpreda; Roy Y. Hori, both of Warsaw, Ind.; Richard F. Kyle, Long Lake, Minn.

[73] Assignee: Zimmer, Inc., Warsaw, Ind.

[21] Appl. No.: 6,327

[22] Filed: Jan. 21, 1993

Related U.S. Application Data

[63] Continuation of Ser. No. 794,289, Nov. 19, 1991, abandoned.

[51] Int. Cl.⁶ ................... A61F 2/32; A61F 2/34
[52] U.S. Cl. ................... 623/23; 623/16; 623/18
[58] Field of Search ................... 623/22, 23, 18

[56] References Cited

U.S. PATENT DOCUMENTS

| | | | |
|---|---|---|---|
| Re. 32,471 | 8/1987 | Keller | 53/23 |
| 4,435,854 | 3/1984 | Keller | 3/1.913 |
| 4,546,501 | 10/1985 | Gustilo et al. | 623/22 X |
| 4,578,081 | 3/1986 | Harder et al. | 623/22 X |
| 4,661,112 | 4/1987 | Muller | 623/22 |
| 4,756,711 | 7/1988 | Mai et al. | 623/16 X |
| 4,770,661 | 9/1988 | Oh | 623/23 |
| 4,790,854 | 12/1988 | Harder et al. | 623/23 |
| 4,792,339 | 12/1988 | Tepi | 623/23 |
| 4,808,186 | 2/1989 | Smith | 623/23 |
| 4,883,491 | 11/1989 | Mallory et al. | 623/23 |
| 4,938,774 | 7/1990 | Tepic | 623/23 |
| 4,944,759 | 7/1990 | Mallory et al. | 623/23 |
| 4,944,761 | 7/1990 | Stuhmer et al. | 623/23 |
| 4,986,834 | 1/1991 | Smith et al. | 623/23 |
| 4,995,883 | 2/1991 | Demane et al. | 623/23 |
| 5,002,578 | 3/1991 | Luman | 623/23 |
| 5,080,685 | 1/1992 | Bolesky et al. | 623/18 X |
| 5,092,899 | 8/1992 | Fortz | 623/23 |
| 5,100,407 | 3/1992 | Conrad et al. | 623/18 X |
| 5,116,379 | 5/1992 | McLardy-Smith | 623/23 |
| 5,181,928 | 1/1993 | Bolesky et al. | 623/22 X |
| 5,258,035 | 11/1993 | Hoffman et al. | 623/23 |
| 5,286,260 | 2/1994 | Bolesky et al. | 623/22 X |
| 5,336,265 | 8/1994 | Serbousek | 623/23 |

FOREIGN PATENT DOCUMENTS

| | | | |
|---|---|---|---|
| 0229578 | 7/1987 | European Pat. Off. | 623/23 |
| 2549717 | 1/1985 | France | A61F 2/32 |
| WO91/18562 | 12/1991 | WIPO | A61F 2/36 |

*Primary Examiner*—David Isabella
*Attorney, Agent, or Firm*—Cary R. Reeves

[57] ABSTRACT

An implant fixation stem has a distal portion with a controlled stiffness. In one embodiment the deflection in response to a given force is equal to other similarly designed stems to give a surgeon consistent implantation feedback regardless of implant size. The deflection is preferably provided via a slot in the stem, the slot length being determined as a function of the stem's moment of inertia. Alternate embodiments provide for flutes of unequal length.

5 Claims, 2 Drawing Sheets

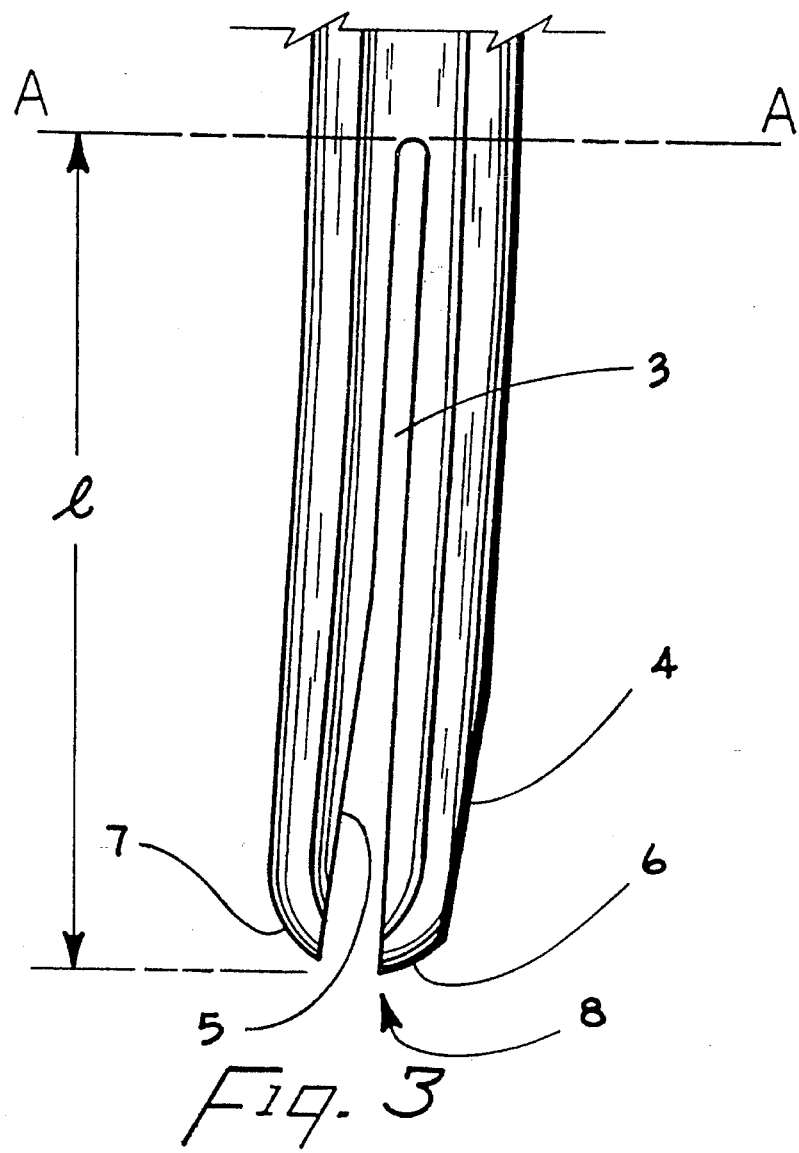
Fig. 3
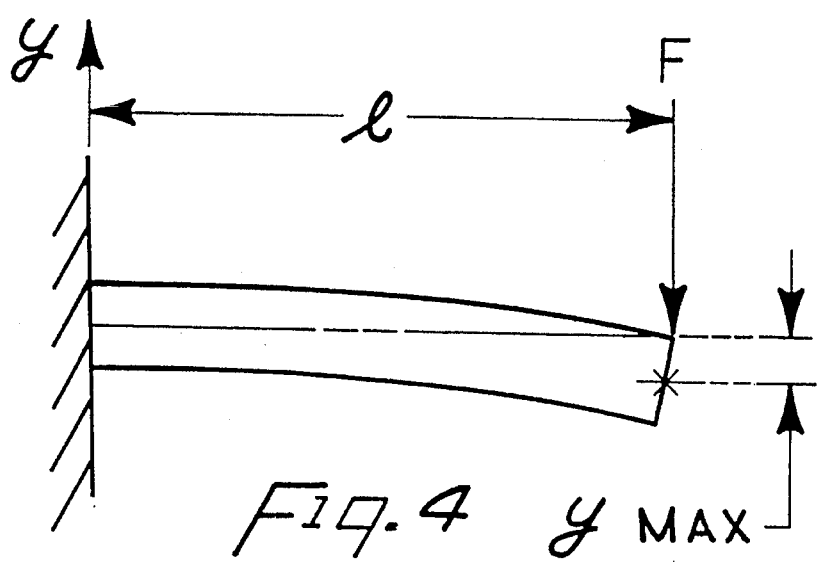
Fig. 4    y MAX

5,507,829

SET OF FIXATION STEMS HAVING SIMILAR STIFFNESS

This is a continuation of application Ser. No. 07/794,289 filed Nov. 19, 1991, now abandoned.

BACKGROUND OF THE INVENTION

The present invention relates to an implant fixation stem such as for a prosthetic hip implant. More specifically this invention is concerned with controlling stem stiffness and stem implantation characteristics.

It is advantageous in hip replacement surgery to use an implant that fills the interior space of a femur as much as possible. To this end, a particular hip stem design is usually provided as a system having a variety of sizes. During surgery, the femur is hollowed with a rasp and the appropriately sized implant is then driven into the hollowed femur. However, the femur is curved so that there exists a tradeoff between the stem filling the femur and the stem being able to traverse the curve without undue resistance to implantation and pressure on the femur. It is known to reduce the stiffness of a stem by various means in order to ease implantation and avoid splitting the femur as it traverses the femoral curve. This is only a partial solution though, because as the stem size increases the stem stiffness increases, generally at an exponential rate. Therefore, larger stems are increasingly more difficult to implant. The prior art has failed to appreciate that it is important not only to control individual implant stiffness, but to control the relative stiffness between implants within an implant system having a range of stem sizes. This is so because as a surgeon is driving a stemmed implant into a hollowed bone he relies on the feedback of how easily the implant enters the hollow bone to determine if femoral damage is imminent and if the implant is well seated. With prior devices the feedback from a small implant is different from that of a large implant, making it difficult for the surgeon to develop a familiarity with the implantation procedure.

SUMMARY OF THE INVENTION

It is therefore an object of this invention to provide a hip stem with controlled stiffness. It is a further object to control the stem stiffness in such a way that the feedback to the surgeon during implantation is uniform for a range of implant sizes thereby enabling the surgeon to develop a familiarity with the implantation procedure and consequently confidence in femoral safety and in seating the implant. It is another object of this invention to provide a hip stem that is easily inserted into the femur. These objects are realized in a hip stem having a slotted distal stem wherein the slot geometry is calculated to provide substantially the same stem deflection in response to a force for all stems in a range of sizes. Alternate embodiments of this hip stem have flutes of varying length in the distal stem to further control stiffness. External and internal chamfers are present to ease insertion of the hip stem into the femur and to prevent metal-on-metal wear.

BRIEF DESCRIPTION OF THE DRAWING

In the drawings:

FIG. 3 is a detail view of the distal end of the hip implant of FIG. 1.

FIG. 4 is a diagram depicting a simple cantilever beam model upon which the calculations of this disclosure are based.

DETAILED DESCRIPTION OF THE INVENTION

Figures 1, 2:
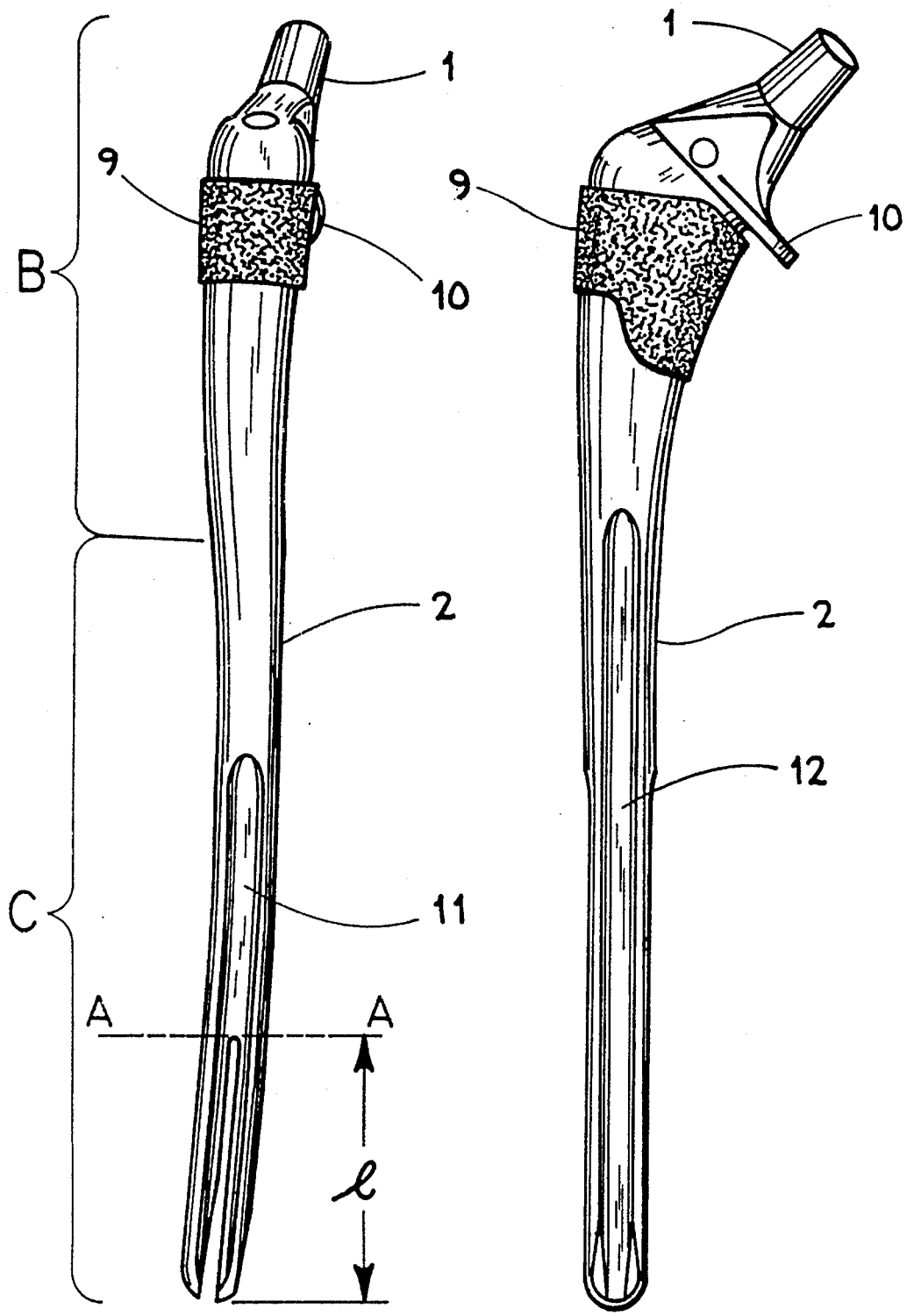
FIG. 1 is a lateral view of a right femoral hip implant.
FIG. 2 is an anterior view of the femoral hip implant of FIG. 1.

Referring to the figures, a femoral hip implant according to this invention has a neck 1 and a stem 2 distal to the neck. The stem 2 is designed to have a predetermined deflection in response to a predetermined force that is substantially the same as that of other similarly designed implants regardless of their respective sizes. This uniform stiffness causes all of the similar implants to present to a surgeon the same resistance to implantation so that the surgeon may be confident in the safety of a femur undergoing implantation and in the proper seating of the implant. In a preferred embodiment, the stiffness of the stem is controlled grossly via mass reducing flutes 11 and 12 and precisely via a slot 3. As shown in FIGS. 1 and 2, the lateral flute 11, which is loaded tensilely, is shorter in length than the anterior flute 12. Preferably, the implant contains opposing and corresponding flutes on its posterior and medial aspects. The slot is preferably in the medial-lateral plane of the implant as shown. As the implant is inserted into the femur, one or both sides of the slot 3 may deflect inward to ease insertion. If one side of the slot 3 is modelled as a simple cantilever beam fixed along line A—A, then FIG. 4 diagrams the resulting design problem. In this case $$y_{max} = -\frac{Fl^3}{3EI} \quad (1)$$

where deflection "$y_{max}$" is produced by a force "F" in a beam of length "l" having a material property "E" and a section property "I". An implant designer, knowing a desired deflection "$y_{max}$" for a given force "F", can design a system of implants to have uniform stem stiffness by making the slot 3 length "l" for each implant conform to $$l = \left[ -\frac{3EI}{F} y_{max} \right]^{1/3} \quad (2)$$

Since the force "F" and deflection "$y_{max}$" are held constant for all implants in the system, and assuming all the implants in the system are made of the same material, the slot length is a function of the section property "I" for each implant $$l = fn[I] \quad (3)$$

The preferred implant has an exterior chamfer 4 and an interior chamfer 5 in addition to radii 6 and 7 at the end 8 of the stem 2. The exterior chamfer 4 permits easier insertion of the implant into the femur and allows the implant to move smoothly down the femur. The implant stem 2 is designed to fit closely within the femur. Therefore, it is preferable to limit the length of the exterior chamfer (to approximately 0.800") to provide pronounced relief (of approximately 1.5 mm) at the end 8 of the stem 2 and a rapid transition to the close fit between the stem and the interior of the femur. The exterior chamfer 4 may be the same for all sizes of the implant.

The interior chamfer 5 provides clearance so that the sides of the slot 3 do not touch and thereby limit deflection or allow fretting of the sides against one another. In contrast to the exterior chamfer 4, it is preferable to have a relatively long (approximately one-half the length of the slot 3) interior chamfer 5 to ensure that the s ides of the slot 3 do not contact one another. The internal relief at the end of the slot is sized such that the slot will not close when subjected to a predetermined minimum load "F" (approximately 500 pounds). In order to take full advantage of the improved implantability and fit of this implant, it is preferable to provide regions of curvature "B" and "C" that match the curvature of the femur. In addition, it is preferable to provide porous surfaces 9 to increase fixation strength by tissue ingrowth and a collar 10 to increase implant stability.

While the foregoing has described a preferred embodiment of the present invention, the specific dimensions disclosed are for illustrative purposes only. In addition, the invention can be employed with stemmed implants other than for use in the hip joint. It will be understood by those skilled in the art that various modifications may be made to the preferred embodiment without departing from the spirit and scope of the invention defined by the appended claims.

We claim:

1. A set of stemmed implants for a bone comprising a first stemmed implant and a second stemmed implant, said first stemmed implant having a body, a stem extending from said body, said stem having a predetermined stiffness, said second stemmed implant having a body, a stem extending from said body of said second stemmed implant, said stem of said second stemmed implant having a predetermined stiffness, said body and stem of said first stemmed implant being larger than said body and stem of said second stemmed implant, said predetermined stiffness of said stem of said first stemmed implant being substantially similar to said predetermined stiffness of said stem of said second stemmed implant, the stem of each of said first and second stemmed implants including a slot extending through the stem, the slot separating two cantilevered sides of the stem.

2. The set of stemmed implants of claim 1 wherein one cantilevered side of said stem is eternally chamfered and the other cantilevered side of said stem is internally chamfered.

3. The set of stemmed implants of claim 1 wherein each of said first and second stemmed implants has a medial-lateral plane corresponding to a medial-lateral plane of the bone when the implant is implanted into the bone, said slot of each of said first and second stemmed implants lies in the medial-lateral plane of the implant.

4. A set of stemmed implants for a bone comprising a first stemmed implant and a second stemmed implant, said first stemmed implant having a body, a stem extending from said body, said stem having a predetermined stiffness, said second stemmed implant having a body, a stem extending from said body of said second stemmed implant, said stem of said second stemmed implant having a predetermined stiffness, said body and stem of said first stemmed implant being larger than said body and stem of said second stemmed implant, said predetermined stiffness of said stem of said first stemmed implant being substantially similar to said predetermined stiffness of said stem of said second stemmed implant, the stem of the first stemmed implant including a slot, the size of the slot in the first stemmed implant being determined as a function of a section property of the stem of the first stemmed implant so as to produce the predetermined stiffness of the stem of the first stemmed implant and the stem of the second stemmed implant including a slot, the size of the slot in the second stemmed implant being determined as a function of a section property of the stem of the second stemmed implant so as to produce the predetermined stiffness of the stem of the second stemmed implant such that since the body and stem of the first stemmed implant are larger than the body and stem of the second stemmed implant, the slot in the stem of the first stemmed implant is a different size than the slot in the stem of the second stemmed implant.

5. A set of stemmed implants for a bone comprising a first stemmed implant and a second stemmed implant, the first stemmed implant having a body and a stem extending from the body, the stem containing a slot extending through the stem separating two cantilevered sides of the stem and the slot having a length, one of the cantilevered sides of the stem being able to be deflected inwardly toward the other cantilevered side in response to a predetermined force, the second stemmed implant having a body and a stem extending from the body, the stem containing a slot extending through the stem separating two cantilevered sides of the stem and the slot having a length, one of the cantilevered sides of the stem being able to be deflected inwardly toward the other cantilevered side in response to the predetermined force, the stem of the first stemmed implant being larger than the stem of the second stemmed implant, the length of the slot in the first stemmed implant being longer than the length of the slot in the second stemmed implant, the predetermined amount of deflection of the one cantilevered side of the stem of the first stemmed implant in response to the predetermined force being substantially similar to the predetermined amount of deflection of the one cantilevered side of the stem of the second stemmed implant in response to the predetermined force.

* * * * *